US00PP35861P3

(12) United States Plant Patent
Olesen

(10) Patent No.: US PP35,861 P3
(45) Date of Patent: Jun. 11, 2024

(54) MINIATURE ROSE PLANT NAMED 'POULTY031'

(50) Latin Name: *Rosa hybrida*
Varietal Denomination: Poulty031

(71) Applicant: Mogens Nyegaard Olesen, Fredensborg (DK)

(72) Inventor: Mogens Nyegaard Olesen, Fredensborg (DK)

(73) Assignee: POULSER ROSER A/S, Fredensborg (DK)

( * ) Notice: Subject to any disclaimer, the term of this patent is extended or adjusted under 35 U.S.C. 154(b) by 0 days.

(21) Appl. No.: 18/445,494

(22) Filed: Sep. 8, 2023

(65) Prior Publication Data

US 2024/0107908 P1 Mar. 28, 2024

(30) Foreign Application Priority Data

Sep. 30, 2022 (QZ) ..... PBR 2022/2175

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./101, 116
See application file for complete search history.

*Primary Examiner* — Susan McCormick Ewoldt

(57) ABSTRACT

A new garden rose plant of the Miniature class which has abundant, yellow and red stripe flowers and attractive foliage. This new and distinct variety has shown to be uniform and stable in the resulting generations from asexual propagation.

1 Drawing Sheet

Botanical designation: *Rosa hybrida.*
Variety denomination: 'Poulty031'.

This application claims priority to Plant Breeder's Rights Application Number 2022/2175, which was filed at the Community Plant Variety Rights Office in the European Union on Sep. 30, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulty031', originated as a single seedling from the stated cross.

The new variety may be distinguished from its male pollen parent and female seed parent primarily by the following characteristics. The male pollen parent plant has yellow flowers while the new variety has yellow and red stripe flowers. The female seed parent plant has pink flowers with white stripes while the new variety has yellow and red stripe flowers.

The objective of the hybridization of this rose variety was to create a new and distinct variety with unique qualities, such as:

1. Uniform and abundant yellow and red stripe flowers;
2. Vigorous, but very compact growth when propagated on its own roots;
3. Exceptional disease resistance.

This combination of qualities is not present in previously available commercial cultivars of this type, known to the inventor, and distinguish 'Poulty031' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulty031' was selected in the spring of 2016 by the inventor as a single plant from the progeny of the aforementioned hybridization.

Asexual reproduction of 'Poulty031' by rooted cuttings was first done by Mogens N. Olesen in the nursery in Fredensborg, Denmark in July, 2016. This initial and other subsequent asexual propagations conducted in controlled environments have demonstrated that the characteristics of 'Poulty031' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty031'. Specifically illustrated in the drawing is a cluster of flower buds on a branch, open flowers viewed from above and the side, flower petals detached, reproductive flower parts, bare stems, and leaves. Plants shown are 1 year old.

DETAILED DESCRIPTION OF THE VARIETY

The following is a description of 'Poulty031', as observed in its growth in an outdoor nursery in Half Moon Bay California. Observed plants are 12 months of age, and were grown on their own roots in 23 cm pots. Color references are made using The Royal Horticultural Society (London, England) Colour Chart, 2001, except where common terms of color are used.

For a comparison, several physical characteristics of the rose variety 'Poulpar084', U.S. Plant Pat. No. 29,875 are compared to the claimed plant. While 'Poulty031' has 25 flower petals, 'Poulpar084' has 60 flower petals. The claimed plant has flowers with strong perfume, while the comparison variety has a moderate floral scent. Open flowers of 'Poulty031' are generally Yellow Group 4B with streaks the colour of Red Group 53B while 'Poulpar084' has a general tonality of Yellow Group 13B.

FLOWER AND FLOWER BUD

Blooming habit: Continuous.

Flower bud:

- *Size.*—Upon opening, 22 mm in length from base of receptacle to end of bud. Bud diameter is 12 mm.
- *Bud form.*—Ovoid.
- *Bud color.*—As sepals divide petals are Yellow Group 12B with intonations of Red Group 43B.
- *Sepal inner surface.*—Color: Yellow-Green Group 146D. Surface: Lightly pubescent.
- *Sepal outer surface.*—Color: Yellow-Green Group 144A with intonations of Greyed-Red Group 180B. Texture: Smooth.
- *Sepal shape.*—Apex: Cirrhose. Base: Flat at union with receptacle.
- *Sepal margin.*—Margins have no foliaceous appendages on three of the five sepals.
- *Sepal size.*—21 mm long, 5 mm wide.
- *Receptacle.*—Texture: Smooth. Size: 6 mm in height, 5 mm wide. Color: Yellow-Green Group 144A. Shape: Campanulate.
- *Pedicel.*—Surface: Smooth. Length: About 27 mm. Diameter: 2 mm on average. Color: Yellow-Green Group 144A with intonations of Greyed-Red Group 182A. Strength: Strong.
- *Peduncle.*—Length: 1 to 3 cm. Diameter: About 3 mm. Color: Yellow-Green Group 145A. Texture: Smooth.

Flower bud development: Flower buds are borne single, or in clusters of about 5 flower buds per stem.

Flower bloom:

- *Fragrance.*—Strong rose perfume.
- *Duration.*—The blooms have a duration on the plant of approximately 19 days. Petals fall cleanly away from plant after flowers have fully matured.
- *Size.*—Flower diameter is 40 mm when open. Flower depth is 15 mm.
- *Flower shape.*—Rosette with many slightly overlapping petals of different sizes.
- *Shape of flower, side view.*—The upper portion is rounded. The lower portion is flat.

Petalage: Under normal conditions, flowers have about 25 petals.

General tonality of flower: Open flowers are Yellow Group 4B with streaks the colour of Red Group 53B.

Petal color:

- *Upon opening and after opening, inner and outer petals.*—Upper surface: Yellow Group 4B with streaks of Red Group 53D. Lower surface: Yellow Group 8C with streaks Red Group 54B.

Petals:

- *Petal reflex.*—Somewhat reflexed.
- *Margin.*—Entire and uniform. Moderate undulations.
- *Shape.*—Broad and elliptic. Apex shape: Rounded. Base shape: Acute.
- *Size.*—21 mm (l)×19 mm (w).
- *Texture.*—Smooth.
- *Thickness.*—Average.

Petaloids:

- *Size.*—15 mm (l) by 5 mm (w).
- *Quantity.*—3 or 4.
- *Shape.*—Elliptical with an acute base and rounded apices.
- *Color.*—Yellow Group 4B with streaks of Red Group 53D on the upper surface. Lower surface is Yellow Group 8C with streaks Red Group 54B.

Reproductive flower parts:

- *Pollen.*—None observed.
- *Anthers.*—Size: 1 mm in length. Color: Greyed-Orange Group 163A. Quantity: 25 on average.
- *Filaments.*—Color: Yellow Group 12A with intonations of Orange Group 25B. Length: 7 mm.
- *Pistils.*—Length: 5 mm. Quantity: 15 on average.
- *Stigmas.*—Color: Red Group 55C.
- *Styles.*—Color: Red Group 55C.
- *Location of stigmas.*—Inferior in location relative to the length of the filaments and the height of the anthers.
- *Hips.*—None Observed.

PLANT

Plant growth: Upright, bushy. Plants are 33 cm in height and 33 cm wide.

Stems:

- *Color of juvenile growth.*—Yellow-Green Group 144A.
- *Color of mature growth.*—Yellow-Green Group 146B.
- *Length.*—Canes are about 20 cm from the base of the plant to the flowering portion.
- *Diameter.*—About 6 mm.
- *Internodes.*—On mature canes about 20 mm between nodes.
- *Surface texture.*—Young wood: Smooth. Older wood: Smooth.

Long prickles:

- *Incidence.*—6 to 8 prickles per 10 cm of stem.
- *Size.*—Average length of prickles on mature stems is 3 mm.
- *Shape.*—Upper portion is linear. Lower portion is concave.
- *Color.*—Juvenile prickles: Greyed-Red Group 180C. Mature prickles: Greyed-Red Group 180C.

Plant foliage:

- *Compound leaf.*—74 mm (l)×37 (w).
- *Quantity.*—3 leaves per 10 cm of stem on average.
- *Leaf bearing angle to the stem.*—45 degrees.
- *Color of juvenile foliage.*—Upper side: Yellow-Green Group 144A. Lower side: Yellow-Green Group 144B.
- *Color of mature foliage.*—Upper side: Yellow-Green Group 146A. Lower side: Yellow-Green Group 146B.

Plant leaves and leaflets:

- *Stipules.*—Size: 14 mm long, 2 mm wide. Quantity: 2 per compound leaf. Shape: Linear, slightly broad based with outward extending apices. Margins:

Finely serrated. Color: Yellow-Green Group 144A with light intonations of Greyed-Red Group 180B.

*Petiole*.—Length: 11 mm. Diameter: 1.5 mm. Upper surface color: Yellow-Green Group 144A. Lower surface color: Yellow-Green Group 144A.

*Rachis*.—Length: 27 mm. Upper surface color: with intonations of Greyed-Purple Group 183A. Lower surface color:

*Leaflet*.—Quantity: Normally 5, occasionally 7 leaflets. Margins: Serrated. Size: Terminal leaflets are about 25 mm long, 18 mm wide. Shape: Generally elliptical to rounded. Base: Rounded. Apex: Acute or acuminated. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty031' substantially as described and illustrated herein.

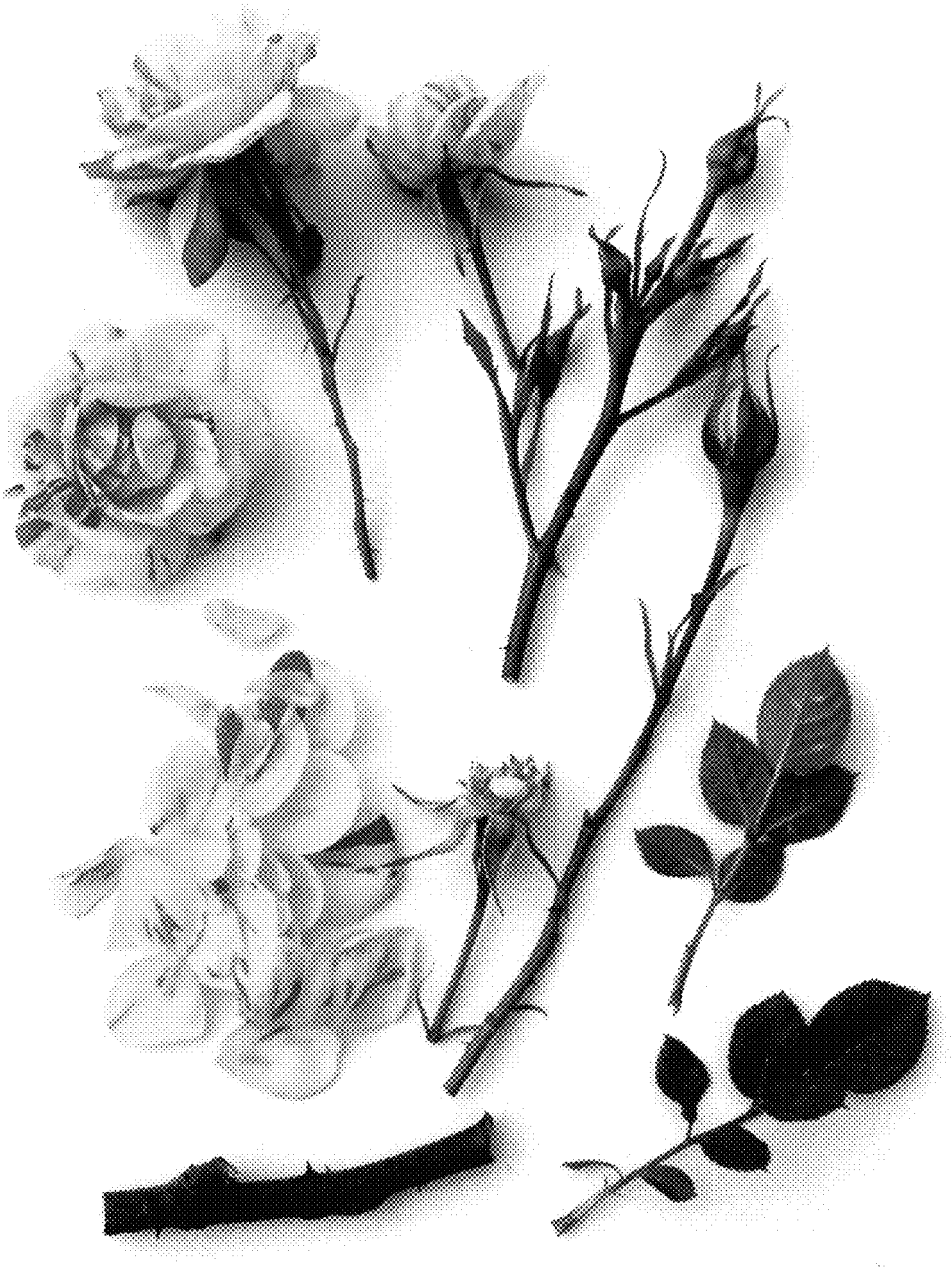

* * * * *